United States Patent [19]

Af Ekenstam et al.

[11] 4,061,625
[45] Dec. 6, 1977

[54] NOVEL CHROMOGENIC THROMBIN SUBSTRATES

[75] Inventors: Bo Thuresson Af Ekenstam, Molndal; Leif Eric Aurell; Karl Göran Claeson, both of Saro; Birgitta Gunilla Karlsson, Molndal, all of Sweden

[73] Assignee: AB Kabi, Stockholm, Sweden

[21] Appl. No.: 697,003

[22] Filed: June 17, 1976

[51] Int. Cl.² .................................... C07C 103/52
[52] U.S. Cl. ...................... 260/112.5 R; 195/103.5 R; 195/99
[58] Field of Search .................. 260/112.5 R; 424/177

[56] References Cited

U.S. PATENT DOCUMENTS

| | | | |
|---|---|---|---|
| 3,388,113 | 6/1968 | Guttmann et al. | 260/112.5 R |
| 3,778,426 | 12/1973 | Naffar | 260/112.5 R |
| 3,867,364 | 2/1975 | Umezawa et al. | 260/112.5 R |
| 3,884,896 | 5/1975 | Blomback et al. | 424/177 |
| 3,886,136 | 5/1975 | Claeson et al. | 260/112.5 R |

*Primary Examiner*—Delbert R. Phillips
*Attorney, Agent, or Firm*—Pollock, Vande Sande & Priddy

[57] ABSTRACT

Substrate with high specificity to thrombin and thrombin-like enzymes having the formula:

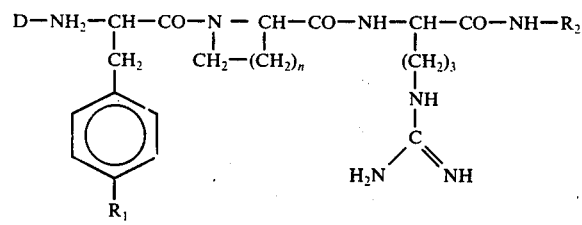

and salts thereof, wherein $R_1$ is H or OH; $R_2$ is nitrophenyl; and $n$ is 1, 2 or 3 provided along with the method of use.

10 Claims, No Drawings

NOVEL CHROMOGENIC THROMBIN SUBSTRATES

The present invention relates to novel chromogenic substrates for thrombin and thrombin-like enzymes. The substrates according to the invention are especially suitable for a quantitative determination of thrombin or for a study of reactions in which thrombin is formed, inhibited or consumed, or for determination of factors which exert an influence or take part in such reactions, e.g. for determination of anti-thrombin, prothrombin and heparin.

Synthetic substrates for enzyme determinations have great advantages as compared to the natural ones, provided that they fulfill certain conditions, such as a great sensitivity for and specificity for the enzyme, a good solubility in water or the biological test liquid and easy detectability of some of the splitting products.

One of the hitherto best substrates for thrombin determination is described in our Swedish Pat. No. 380.257 and consists of the chromogenic tripeptide derivative (as regards the abbreviations cf. page 4):

Bz—Phe—Val—Arg—pNA (S—2160)      A

This has a great sensitivity for thrombin and gives upon enzymatic hydrolysis the chromophoric product p-nitroaniline which easily can be determined spectrophotometrically. S-2160 has, however, a delimitation due to its relatively low solubility (1 mg/ml). A low solubility causes the disadvantage that one has to work very near the saturation limit for the substrate so as to achieve a satisfactory substrate concentration. In enzyme determination in different biological systems a precipitation of the substrate as such can occur or a combined protein/substrate precipitation. The said precipitations will cause erroneous spectrophotometer readings and thus erroneous enzyme determinations. The enzyme substrate S-2160 becomes considerably more soluble if the benzoyl group is replaced with H, thus:

H—Phe—Val—Arg—pNA      B

The now free protonized amino group on Phe increases the solubility, but causes also that the velocity with which thrombin splits the substrate decreases heavily, about 30 times (cf. Table I). Further, the substrate can, in a biological test solution, in a non-desired way be decomposed from the N-terminal end by amino peptidases.

According to the present invention the substrate according to formula B has been modified by exchanging Val for a cyclic imino acid (Aze, Pro or Pip) and L-Phe with D-Phe. As expected the substrates so obtained are still very soluble but quite surprisingly the activity against thrombin is not decreased but instead it is 30–50 times higher than the activity for the corresponding substrate with solely L-amino acids (Table I). Further, the novel substrates are about 400% more active than S-2160. The N-terminal D-amino acid also prevents a non-desired attack by amino peptidases since the latter are specific for L-amino acids. The novel chromogenic substrates according to the invention are characterized by the following general formula:

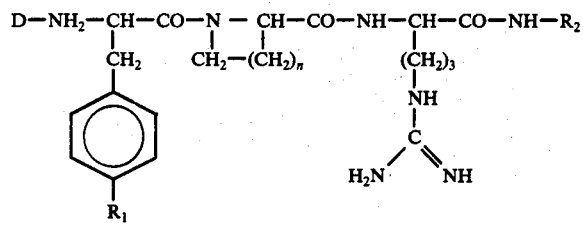

or salts thereof, wherein $R_1$ can be hydrogen or hydroxy. $R_2$ can be chosen among nitrophenyl, naphthyl, nitronaphthyl, methoxynaphthyl, quinolyl or nitroquinolyl, and $n$ can be 1, 2 or 3.

For the synthesis of the novel chromogenic enzyme substrates conventional protective groups and coupling methods are used all of which are well-known within the peptide chemistry.

As an α-amino protective group carboxybenzoxy or t-butyloxycarbonyl groups can be used with advantage or any group related thereto such as for instance p-methoxy, p-nitro or p-methoxyphenylazo carbobenzoxy.

As a protection for the δ-guanido group of the arginyl group it is advantageous to use protonization, an $NO_2$-group or a p-toluene-sulphonyl group.

As protection for the hydroxy group in the tyrosine group it is of advantage to use a t-butyl or benzyl group. As a splittable carboxy protective group it is suitable to use methyl, ethyl or benzyl ester.

The coupling between two amino acids or a dipeptide and an amino acid is achieved by activation of the α-carboxy group. The activated derivative can either by isolated or generated in situ and can be for instance p-nitrophenyl, trichlorophenyl, pentachlorophenyl or N-hydroxysuccinimide ester, symmetric or asymmetric anhydride, acid azid, or N-hydroxybenzotriazole ester.

The principle for the synthesis can be a stepwise coupling of the amino acids to the C-terminal arginyl group, either already provided with a coupled chromophoric group which functions as a carboxy protective group or provided with a splittable carboxy protective group, and the chromophoric group is then coupled to the protected tripeptide derivative, or alternatively it is possible to synthesize the N-terminal dipeptide fragment per se which then is coupled to the arginyl group with or without a chromophoric group according to the statements above.

Independently of the chosen principle a purification of intermediary and end products by gel filtration chromatography is suitable since this will enable a rapid synthesis work and gives maximal yields.

TLC analysis has been made partly of eluates from GPC and partly of evaporated and dried end and intermediary products.

The invention is described in more detail in the following non-limiting specific examples.

| Abbreviations | |
|---|---|
| Amino acids (if not otherwise stated the L-form is meant): | |
| Arg | = Arginine |
| Aze | = 2-Azetidine carboxylic acid |
| Phe | = Phenylalanine |
| Pip | = Pipecolinic acid |
| Pro | = Proline |
| Val | = Valine |
| AcOH | = Acetic acid |
| Bz | = Benzoyl |
| Cbo- | = Carbobenzoxy- |

-continued

Abbreviations

Amino acids (if not otherwise stated the L-form is meant):

| | |
|---|---|
| DMF | = Dimethylformamide |
| Et₃N | = Triethylamine |
| EtOAc | = Ethylacetate |
| HMPTA | = N, N, N', N', N'', N''-hexamethylphosphoric acid triamide |
| GPC | = Gel filtration chromatography |
| MeOH | = Methanol |
| -OpNP | = p-nitrophenoxy |
| -pNA | = p-nitroanilide |
| TLC | = Thin-layer chromatography |

Thin-layer chromatography:

For TLC-analysis preprepared glass plates are used with silica gel $F_{254}$ (Merck) as absorption agent. The solvent systems used are the following:

$P_1$: chloroform: MeOH 9:1 (volume ratio)

A : n-butanol : AcOH : water 3:2:1 (volume ratio)

After finished chromatography the plate is studied in UV-light (254 nm) and development is made subsequently with chlorine/o-toluidine reagent according to common practice. When a "homogenous product according to TLC" is stated the analysis is performed on an amount of µg. The $R_f$ values stated are results from separate chromatographic procedures.

The gel Sephadex ® G-15 used for the gel filtration is a crosslinked dextran gel. The gel Sephadex ® LH-20 is a hydroxypropylated crosslinked dextran gel. The ion exchanger Sephadex ® QAE-25 used is a crosslinked dextran gel with diethyl-(2-hydroxy-propyl)-aminoethyl as functional group. These gels are from Pharmacia Fine Chemicals, Uppsala, Sweden.

Description of the synthesis

I. Cbo—Arg(NO₂)pNA 35.3 g (10 mmol) of dry Cbo—Arg(NO₂)—OH are dissolved in 200 ml of dry freshly distilled HMPTA at room temperature, whereupon 10.1 g (100 mmol) of Et₃N and 24.6 g (150 mmol) p-nitrophenyl isocyanate is added during stirring and moisture-free conditions. After a reaction time of 24 h the solution is poured down in 2l of 2% sodiumbicarbonate solution under stirring. The precipitation formed is removed by filtration and washed with 2% bicarbonate solution, water, 0.5 N HCl (aq) and water and finally dried. The raw product is extracted with warm MeOH and difficultly soluble by-products are filtrated. The filtrate is purified by chromatography on a column of Sephadex ® LH-20, swelled in and eluated with MeOH. Yield: 29.8 g (63%) Analysis: Homogenous according to TLC in $P_1$ ($R_f$ 0.34) $[\alpha]_D^{24}$ + 20.5° (c 1.9, DMF)

II. Cbo—Pro—Arg(NO₂)-pNA 4.8 g (10 mmol) of Cbo—Arg(NO₂)—pNA are slurried in 25 ml of dry AcOH, whereupon 15 ml of 5.6 N HBr in AcOH are added. After a reaction period of 50 min at room temperature the solution is poured under vigorous stirring into 300 ml of dry ether. The ether phase is sucked from the precipitation obtained and the precipitation is washed with 2 portions of 100 ml of ether each. The HBr.H—Arg(NO₂)—pNA thus obtained is dried in vacuum over NaOH at 40° C for 16 h. It is subsequently dissolved in 25 ml of DMF and the solution is cooled to +10° C. Now Et₃N is added in an amount sufficient for giving a moist pH-paper kept immediately above the surface of the solution a weakly basic reaction (1.9 ml). Precipitated Et₃N.HBr is removed by filtration and 4.1 g (11 mmol) of Cbo-Pro-OpNP are added. After 1 h further 0.7 ml Et₃N are added and also after 4 h. The solution is allowed to adjust to room temperature over the night. So as to avoid that the excess of Cbo-Pro-OpNP contaminates the end product during GPC since they have similar eluation volumes in the chromatographic system used 0.5 ml (5 mmol) of n-butyl amine is added. After 30 min 10 mmol of diluted HCl are added, the reaction solution is evaporated on a rotavapor, stirred with a couple of portions of water which is removed by decantation. The residue is dissolved in MeOH and chromatographed on a column of Sephadex⁽ᴿ⁾ LH-20, swelled in and eluated with MeOH. The product obtained is homogenous according to TLC. Yield: 5.5 g (96%) Analysis: TLC in $P_1$ ($R_f$ 0.28) $[\alpha]_D^{24}$ −33.0° (c 1.0, DMF)

III. Cbo-Pip-Arg(NO₂)- pNA

Performed according to II. Yield: 5.1 g (86%) Analysis: Homogenous according to TLC in $P_1$ ($R_f$ 0.30) $[\alpha]_D^{24}$ −26.2° (c 1.0, DMF)

IV. Cbo—Phe—Pip—Arg(NO₂)—pNA 2.9 g (5 mmol) Cbo—Pip—Arg(NO₂)—pNA are dicarbobenzoxylated in HBr in AcOH, precipitated and washed with ether and dried according to II. HBr—H—Pip—Arg(NO₂)—pNA is then dissolved in 15 ml of DMF. The solution is cooled to −10° C, made weakly basic with 0.9 ml of Et₃N and filtrated. 3.0 g (7.15 mmol) of Cbo—Phe—OpNP are added and then 0.65 g (5 mmol) of N-hydroxybenzotriazole as a catalyst. After 1 h further 0.35 ml of Et₃N is added and the same procedure repeated after 4 h. The reaction solution is allowed to increase to room temperature over night. The solution is evaporated to dryness in a rotavapor. The residue is dissolved in EtOAc and treated with 2% sodium bicarbonate solution and water and then evaporated. The residue is now dissolved in MeOH and chromatographed on Sephadex⁽ᴿ⁾ LH-20 swelled and eluated with MeOH. The product obtained is homogenous according to TLC. Yield: 2.7 g (73%) Analysis: TLC in $P_1$ ($R_f$ 0.35) $[\alpha]_D^{24}$ −32.9° (c 1.0, DMF)

V. Cbo—D—Phe—Pip—Arg(NO₂)—pNA

Performed according to IV. Yield: 2.6 g (70%) Analysis: Homogenous according to TLC in $P_1$ ($R_f$ 0.44) $[\alpha]_D^{24}$ −38.4° (c 1.0, DMF)

VI. Cbo—Phe—Pro—Arg(NO₂)—pNA Performed according to IV. Yield: 2.9 g (80%) Analysis: Homogenous according to TLC in $P_1$ ($R_f$ 0.38) $[\alpha]_D^{24}$ −39.2° (c 1.0, DMF)

VII. Cbo—D—Phe—Pro—Arg(NO₂)—pNA Performed according to IV. Yield: 3.1 g (85%) Analysis: Homogenous according to TLC in $P_1$ ($R_f$ 0.46) $[\alpha]_D^{24}$ −6.2° (c 1.0, DMF)

VIII. H—D—Phe—Pro—Arg—pNA.2HCl 175 mg (0.246 mmol) Cbo—D—Phe—Pro—Arg-(NO₂)—pNA is deprotected by reaction with 5 ml of dry HF in the presence of 0.3 ml of anisole in an apparatus intended for this purpose according to Sakakibara for 60 min at 0° C. After finished reaction and after distillation of all HF the raw product is purified and submitted to ion exchange in two steps:

a. GPC on a column of Sephadex⁽ᴿ⁾ G-15, swollen in 33% AcOH in water, with the same medium as dissolving and eluation medium. The pure product is freeze dried from AcOH (aq).

b. Ion exchange on a column of Sephadex⁽ᴿ⁾ QAE-25 in the chloride form, swollen in MeOH:water (95:5) with the same medium as dissolving and eluating medium. The pure product is freeze dried from water.

Yield 120 mg (80%) Analysis: Homogenous according to TLC in A (R$_f$ 0.29) Chloride content 11.53% (theoretically 11.6%) [α]$_D^{24}$ −122° (c 0.5, 50% AcOH (aq))

IX. H—Phe—Pro—Arg—pNA.2HCl

Performed according to VIII. Yield (71%) Analysis: Homogenous according to TLC in A (R$_f$ 0.22) Chloride content 11.0% (theoretically 11.6%) [α]$_D^{24}$ −73.6° (c 0.5, 50% AcOH (aq))

X. H—D—Phe—Pip—Arg—pNA.2HCl

Performed according to VIII. Yield: (72%) Analysis: Homogenous according to TLC in A (R$_f$ 0.44) Chloride content 11.4% (theoretically 11.3%) [α]$_D^{24}$ −109° (c 0.4, 50% AcOH (aq))

XI. H—Phe—Pip—Arg—pNA.2HCl Performed according to VIII. Yield: (55%) Analysis: Homogenous according to TLC in A (R$_f$ 0.41) Chloride content 11.3% (theoretically 11.3%) [α]$_D^{24}$ −80.3° (c 0.5, 50% AcOH (aq))

XII. Cbo—D—Tyr(OBzl)—Pip—Arg(NO$_2$)—pNA Performed according to IV. Yield: 3.2 g (75%) Analysis: Homogenous according to TLC in P$_1$ (R$_f$ 0.50)

XIII. H—D—Tyr—Pip—Arg—pNA

Performed according to VIII. Yield: (68%) Analysis: Homogenous according to TLC in P$_1$ (R$_f$ 0.44) Chloride content 10.8% (theoretically 11.1%) [α]$_D^{24}$ −75.2° (c 0.5, 50% AcOH (aq))

XIV. Cbo—Aza—Arg(NO$_2$)—pNA Performed according to II. Yield: 4.2 g (75%) Analysis: Homegenous according to TLC in P$_1$ (R$_f$ 0.27)

XV. Cbo—D—Phe—Aze—Arg(NO$_2$)—pNA

Performed according to IV. Yield 2.4 g (69%) Analysis: Homogenous according to TLC in P$_1$ (R$_f$ 0.47)

XVI. H—D—Phe—Aze—Arg—pNA·2HCl

Performed according to VIII. Yield: (71%) Analysis: Homogenous according to TLC in A (R$_f$ 0.21) Chloride content 11.6% (theoretically 11.9%) [α]$_D^{24}$ −130° (c 0.5, 50% AcOH)

XVII. Cbo—Arg(NO$_2$)—βNA 7.2 g (20 mmol) of dry Cbo—Arg(NO$_2$)—OH are dissolved in 400 ml of THF. 2.0 g (20 mmol) Et$_3$N are added, whereupon the solution is cooled to −10° C under completely moisture free conditions. 2.7 g (20 mmol) of isobutyl-chloroformate dissolved in 20 ml of THF are added to the cooled solution during 10 min, and after another 10 min 344 g (20 mmol) of β-naphthylamine are added. The reaction mixture is allowed to each room temperature and is left at this temperature for 24 h. The reaction mixture is evaporated in vacuum to dryness, is treated 3-5 times with distilled water, 3-5 times with a 5% sodium dicarbonate solution and again 3-5 times with distilled water, after which it is dried in vacuum. The product is dissolved in MeOH and chromatographed on a column of Sephadex$^{(R)}$ LH-20, swelled in and eluated with MeOH. The product obtained is homogenous according to TLC in P$_1$. Yield: 8.1 g (84%) Analysis: Homogenous according to TLC in P$_1$ (R$_f$ 0.40) [α]$_D^{23}$ +7.4° (c 1.0, DMF)

XVIII. Cbo—Pip—Arg(NO$_2$)—αNA

Performed according to II. Yield: 4.8 g (82%) Analysis: Homogenous according to TLC in P$_1$ (R$_f$ 0.36)

XIX. Cbo—D—Phe—Pip—Arg(NO$_2$)—αNA

Performed according to IV. Yield: 2.6 g (71%) Analysis: Homogenous according to TLC in P$_1$ (R$_f$ 0.48)

XX. H—D—Phe—Pip—Arg—αNA·2HCl

Performed according to VIII. Yield: (68%) Analysis: Homogenous according to TLC in A (R$_f$ 0.44) Chloride content 11.2% (theoretically 11.3%) [α]$_D^{24}$ −105° (c 0.5, 50% AcOH (aq))

XXI. Cbo—Arg(NO$_2$)—αNA (4—OMe)

Performed according to XVII. Yield: 7.1 g (70%) Analysis: Homogenous according to TLC in P$_1$ (R$_f$ 0.42)

XXII. Cbo—Pip—ARG(NO$_2$)—αNA (4—OMe)

Performed according to II. Yield: 4.9 g (79%) Analysis: Homogenous according to TLC in P$_1$ (R$_f$ 0.38)

XXIII. Cbo—D—Phe—Pip—Arg(NO$_2$)—αNA (4—OMe)

Performed according to IV. Yield: 2.7 g (70%) Analysis: Homogenous according to TLC in P$_1$ (R$_f$ 0.51)

XXIV. H—D—Phe—Pip—Arg—αNA (4—OMe)·2HCl

Performed according to VIII. Yield: (64%) Analysis: Homogenous according to TLC in A (R$_f$ 0.44) Chloride content 10.4% (theoretically 10.7%) [α]$_D^{24}$ −102° (c 0.5, 50% AcOH (aq))

Determination of thrombin by chromogenic substrates

The substrates prepared according to the examples are used for determination of thrombin as stated below.

The determnation principle is based upon the fact that the splitting product formed by enzymatic hydrolysis has a UV-spectrum which is essentially different from that of the substrate. Thus, the substrate according to Example X, H—D—Phe—Pip—Aet—pNA, has an absorption maximum at 315 nm and the molar extinction coefficient of 12500. At 405 nm the absorption of the substrate has almost completely stopped. p-Nitroaniline, split off from the substrate during the enzymatic hydrolysis, has an absorption maximum at 380 nm and a molar extinction coefficient of 13200 which at 405 nm only had decreased to 9620. By spectrophotometrical determination at 405 nm it is thus possible to easily follow the amount of p-nitroaniline formed, which is proportional to the degree of the enzyamtic hydrolysis which in its turn is determined by the active amount of thrombin. For other substrates according to the invention rather identical conditions exist and for this reason the determinations have consistently been made at 405 nm.

Table I shows a comparison of the relative reaction velocities between the previously mentioned thrombin substrate S-2160, its non-benzoylated form and substrate according to the invention. This table clearly shows the superiority of the substrates according to the invention. They react 4 times more rapidly with thrombin than the previously set substrate, S-2160, and are further about 10 times more soluble in water than S-2160.

|  | Substrate | Rel. reaction velocity | Solubility in H$_2$O (mg/ml) |
|---|---|---|---|
| A (S-2160) | Bz-Phe-Val-Arg-pNA | 100 | 0.1 |
| B | H-Phe-Val-Arg-pNA | 3 | 1 |
| IX | H-Phe-Pro-Arg-pNA | 15 | 1 |
| VIII | H-D-Phe-Pro-Arg-pNA | 400 | 3 |
| XI | H-Phe-Pip-Arg-pNA | 9 | 1 |
| X | H-D-Phe-Pip-Arg-pNA | 420 | 3 |

Table I

Relative reactions velocity between thrombin (0.4 NIH/ml) and substrate (0.1 μmol/ml).

What is claimed is:

1. Diagnostically active chromogenic substrate with a high specificity to thrombin and thrombin-like enzymes having the general formula:

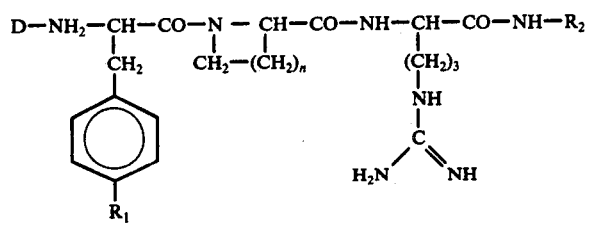

and salts thereof, wherein $R_1$ is hydrogen or hydroxy, $R_2$ is nitrophenyl, and $n$ is 1, 2 or 3.

2. The substrate of claim 1 wherein $R_1$ is hydrogen.
3. The substrate of claim 1 wherein $R_1$ is hydroxy.
4. The substrate of claim 1 wherein $n$ is 1.
5. The substrate of claim 1 wherein $n$ is 2.
6. The substrate of claim 1 wherein $n$ is 3.
7. The substrate of claim 1 which is H—D—Phe—Pro-Arg—P—NA or salt thereof.
8. The substrate of claim 1 which is H—D—Phe—Pip—Art—pNA or salt thereof.
9. The substrate of claim 1 which is H—D—Phe—Aze—Arg—pNA or salt thereof.
10. The substrate of claim 1 which is H—D—Tyr—Pip—Arg—pNA or salt thereof.

* * * * *

UNITED STATES PATENT AND TRADEMARK OFFICE
CERTIFICATE OF CORRECTION

PATENT NO. : 4,061,625
DATED : December 6, 1977
INVENTOR(S) : Bo Thuresson af Ekenstam et al It is certified that error appears in the above-identified patent and that said Letters Patent are hereby corrected as shown below:

Column 3, line 36, change "10" to -- 100 --.

Column 3, line 42, change "21" to -- 2 1 --.

Column 3, line 63, change "+10°C" to -- -10°C --.

Column 4, line 22, change "dicarbobenzoxylated" to -- decarbobenzoxylated --.

Column 5, line 3, change "(aq)" to -- (aq)) --.

Column 5, line 8, change "(aq)" to -- (aq)) --.

Column 5, line 27, change "Aza" to -- Aze --.

Column 6, line 5, change "ARG" to -- Arg --.

Column 6, line 25, change "Aet" to -- Arg --.

Claim 8, line 2, change "Art" to -- Arg --.

Signed and Sealed this

Ninth Day of January 1979

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,061,625
DATED : December 6, 1977
INVENTOR(S) : Bo Thuresson af Ekenstam et al It is certified that error appears in the above-identified patent and that said Letters Patent are hereby corrected as shown below:

Foreign Application Priority Data:

July 11, 1975   Sweden......................7507975

Signed and Sealed this

Twenty-sixth Day of February 1980

[SEAL]

Attest:

SIDNEY A. DIAMOND

Attesting Officer    Commissioner of Patents and Trademarks